(12) United States Patent
Alici (10) Patent No.: US 12,128,061 B2
(45) Date of Patent: Oct. 29, 2024

(54) RNA CONSTRUCT AND METHODS OF USE THEREOF FOR ENHANCING THE THERAPEUTIC EFFECTS OF CYTOTOXIC CELLS AND STEM CELLS

(71) Applicant: Vycellix, Inc., Tampa, FL (US)

(72) Inventor: Evren Alici, Nykoping (SE)

(73) Assignee: VYCELLIX, INC., Tampa, FL (US)

( * ) Notice: Subject to any disclaimer, the term of this patent is extended or adjusted under 35 U.S.C. 154(b) by 498 days.

(21) Appl. No.: 16/147,844

(22) Filed: Sep. 30, 2018

(65) Prior Publication Data

US 2019/0076463 A1 Mar. 14, 2019

Related U.S. Application Data

(63) Continuation-in-part of application No. PCT/US2017/025656, filed on Apr. 1, 2017.

(60) Provisional application No. 62/316,679, filed on Apr. 1, 2016.

(51) Int. Cl.

| | | |
|---|---|---|
| *A61K 31/7105* | (2006.01) | |
| *A61K 9/127* | (2006.01) | |
| *A61K 31/7115* | (2006.01) | |
| *A61K 38/20* | (2006.01) | |
| *A61P 35/00* | (2006.01) | |
| *C07K 16/28* | (2006.01) | |
| *C07K 16/40* | (2006.01) | |
| *C12N 15/117* | (2010.01) | |

(52) U.S. Cl.
CPC ........ *A61K 31/7105* (2013.01); *A61K 9/1271* (2013.01); *A61K 31/7115* (2013.01); *A61K 38/2013* (2013.01); *A61P 35/00* (2018.01); *C07K 16/28* (2013.01); *C07K 16/40* (2013.01); *C12N 15/117* (2013.01); *C12N 2310/17* (2013.01); *C12N 2310/531* (2013.01); *C12N 2320/30* (2013.01); *C12N 2320/31* (2013.01); *C12N 2320/32* (2013.01)

(58) Field of Classification Search
CPC .......... A61K 35/28; A61P 5/00; A61P 31/112; C12N 15/117; C12N 2310/17; C12N 2310/531; C12N 2320/30; C12N 2320/31; C12N 2320/32
USPC ......... 435/6.1, 91.1, 91.31, 455, 458; 514/1, 514/44 A, 44 R; 536/23.1, 24.5
See application file for complete search history.

(56) References Cited

U.S. PATENT DOCUMENTS

| | | |
|---|---|---|
| 2011/0165123 A1 | 7/2011 | Hartmann et al. |
| 2013/0295129 A1 | 11/2013 | Irvine et al. |
| 2016/0017334 A1 | 1/2016 | Hiscott et al. |

FOREIGN PATENT DOCUMENTS

| | | |
|---|---|---|
| WO | 2015/140172 A2 | 9/2015 |
| WO | 2015/144736 A1 | 10/2015 |
| WO | 2016/011324 A2 | 1/2016 |

OTHER PUBLICATIONS

Beljanski et al., "Enhanced Influenza Virus-Like Particle Vaccination with a Structurally Optimized RIG-I Agonist as Adjuvant," *Journal of Virology*, 89(20): 10612-10624 (2015).
Bhat et al., "Serial killing of tumor cells by human natural killer cells—enhancement by therapeutic antibodies," *PloS One*, 2(3): e326 (2007).
Chiang et al., "Sequence-Specific Modifications Enhance the Broad-Spectrum Antiviral Response Activated by RIG-I Agonists," *Journal of Virology*, 89(15): 8011-8025 (2015).
Goubau et al., "Antiviral immunity via RIG-I-mediated recognition of RNA bearing 5'-diphosphates," *Nature*, 514(7522): 372-375 (2014).
Grandvaux et al., "Transcriptional profiling of interferon regulatory factor 3 target genes: direct involvement in the regulation of interferon-stimulated genes," *Journal of Virology*, 76(11): 5532-5539 (2002).
Henkart, P.A. "Mechanism of lymphocyte-mediated cytotoxicity," *Annu Rev Immunol*, 3: 31-58 (1985).
Hornung et al., "5'-Triphosphate RNA is the ligand for RIG-1," *Science*, 314(5801): 994-997 (2006).
Karre et al., "Selective rejection of H-2-deficient lymphoma variants suggests alternative immune defense strategy," *Nature*, 319(6055): 675-678 (1986).
Kawai et al., "IPS-1, an adaptor triggering RIG-1-and Mda5-mediated type I interferon induction," *Nature Immunology*, 6(10): 981-988 (2005).
Lanier L.L. "On guard—activating NK cell receptors," *Nature Immunology*, 2(1): 23-27 (2001).
Liu et al., "New developments in the induction and antiviral effectors of type I interferon," *Current Opinion in Immunology*, 23(1): 57-64. (2011).
Shu et al., "Thermodynamically stable RNA three-way junction for constructing multifunctional nanoparticles for delivery of therapeutics," *Nature Nanotechnology*, 6(10): 658-667 (2011).
Takeuchi et al., "Pattern recognition receptors and inflammation," *Cell*, 140(6): 805-820 (2010).
International Search Report issued Jul. 6, 2017 in PCT/US2017/025656.

(Continued)

*Primary Examiner* — Jane J Zara
(74) *Attorney, Agent, or Firm* — GREENBLUM & BERNSTEIN, P.L.C.

(57) ABSTRACT

The present invention comprises Rig I agonists for enhancing the effects of cytotoxic cells and stem Cells. The Rig I agonists can be used in vivo as small molecule therapeutics or in vitro to enhance cells for adoptive cell transfer. Applications include cancer therapy, immune system enhancement, chronic viral infection and treatment of viral induced inflammation and enhancement of virus based therapies.

17 Claims, 5 Drawing Sheets

Specification includes a Sequence Listing.

(56) References Cited

OTHER PUBLICATIONS

International Preliminary Report on Patentability dated Oct. 2, 2018 including Written Opinion dated Jul. 6, 2017 in PCT/US2017/025656.
Office Action issued Mar. 30, 2023 in Australian Patent Application No. 2017240250.
Goulet et al., "Systems Analysis of a RIG-I Agonist Inducing Broad Spectrum Inhibition of Virus Infectivity," *PLOS Pathogens*, vol. 9, No. 4, e1003298, DOI: 10.1371/journal.ppat.1003298 [1] (19 pages) (2013).
Liu et al., "Influenza A Virus Panhandle Structure is Directly Involved in RIG-I Activation and Interferon Induction," *Journal of Virology*, vol. 89, No. 11, pp. 6067-6079, XP055611114, ISSN: 0022-538X, DOI: 10.1128/JVI.00232-15 [1] (2015).
Office Action dated Jan. 3, 2022 in Israeli patent application No. 261996, with partial English translation.
Office Action dated Nov. 17, 2022 in Israeli patent application No. 261996.
Office Action dated Oct. 11, 2023 in Israeli patent application No. 261996.
Office Action dated Mar. 21, 2023 in Canadian patent application No. 3019577.
Supplementary European Search Report dated Aug. 9, 2019 in European patent application No. 17776891.
Office Action dated Jan. 27, 2021 in Indian patent application No. 201817040944.
Office Action dated Sep. 14, 2023 in Indian patent application No. 201817040944.
Notice of Preliminary Rejection issued in Korean Application No. 10-2022-7035268, dated Jan. 18, 2023, along with an English language translation.
Office Action dated Sep. 9, 2024 issued in Korean patent application No. 10-2024-7000748, with English machine translation thereof.
Yan et al., "Identification of CD90 as a marker for lung cancer stem cells in A549 and H446 cell lines," *Oncology Reports*, 30: 2733-2740, 2013.

RNA CONSTRUCT AND METHODS OF USE THEREOF FOR ENHANCING THE THERAPEUTIC EFFECTS OF CYTOTOXIC CELLS AND STEM CELLS

PRIORITY AND INCORPORATION BY REFERENCE

This application is a continuation in part of Patent Cooperation Treaty application number PCT/US17/25656 filed on Apr. 1, 2017 which claims priority to U.S. provisional patent application No. 62/316,679 filed on Apr. 1, 2016, the contents of which are incorporated by reference. All references cited herein are incorporated by reference.

The instant application contains a Sequence Listing which has been submitted electronically in ASCII format and is hereby incorporated by reference in its entirety. Said ASCII copy, created on Jan. 23, 2024, is named P70373_SL.txt and is 1,639 bytes in size.

BACKGROUND

The efficacy of treatments using natural killer (NK) cells and cytotoxic T cells ("CD8 cells") is impacted by the relative amount ("load") of granzyme B and/or perforin in such cytotoxic cells. Collectively, NK cells and CD8 T cells are referred to as "cytotoxic cells". Cytotoxic cells, including those referred to as adoptive cells, tumor infiltrating lymphocyte cells (TIL), chimeric antigen receptor (CAR) modified cells, and stem cells (herein collectively referred to as adoptive cell transfer), are currently being tested in various clinical trials as a therapeutic treatment, including against numerous cancer types. One of the critical factors for the success of therapeutic treatment with adoptive cell transfer is the load of granzyme B and perforin in NK cells and CD8 T cells.

Cytotoxic cells play a critical role in the early innate response to malignant transformed cells. Cytotoxic cells get activated through various activating receptors on their cell surface or the absence of self-human leukocyte antigen (HLA) on tumor cells (Karre et al., 1986; Lanier, 2001).

The cytotoxicity of both NK and $CD8^+$ T cells is mainly mediated through the release of granzyme B and perforin or the expression of the death receptor ligands such as FasL and TNF-related apoptosis-ligand (TRAIL). Upon activation, lytic granules will be delivered into the intracellular junction formed by the effector and the target cell (Henkart, 1985). Standard practice for adoptive cell transfer, including TIL and CAR genetically modified Cytotoxic Cells, is currently to activate the cells with cytokine exposure in vitro prior to the adoptive transfer. However, the limiting factor is to obtain a sufficient serial killing by each cytotoxic cell, which is highly depended on the overall load with perforin and granzyme B. Moreover, the cells resistance, or lack of resistance, to virus in the transfection process and/or in vivo is a critical factor.

A central step for the load of cytolytic granules is the activation of the intracellular RNA recognition sites such as MDA-5 (melanoma differentiation factor 5) and Rig-I (retinoic acid-inducible gene I), which lead to a direct response of the activated cell.

Viral RNA or synthesized dsRNA molecules with a 5'-triphosphate end (5'ppp) and a size of <100 nucleotides have been found to induce RIG-I (Goubau et al., 2014; Hornung et al., 2006). Furthermore a blunt end base paring at the 5'-end and a length or minimum 20 nucleotides were crucial for optimal binding and activating of RIG-I (Goubau et al., 2014; Hornung et al., 2006). The activated RIG-I interacts with via its CARD domain with the mitochondrial adaptor protein MAVS. Activation of MAVS leads to the activation of the IKK related kinases TBK1 and IKKε, which consequently phosphorylate IRF-3 and IRF-7 as well as activate the NF-κB pathway. Furthermore, this is directly inducing a type I IFN (IFN-β and IFN-α) immune response as well as transcription and secretion of proinflammatory cytokines and selected antiviral genes, such as IFN-stimulated gene 15 (ISG15) and other ISGs (Grandvaux et al., 2002; Kawai et al., 2005; Liu et al., 2011; Takeuchi et al., 2010).

There is a need in the art for an RNA construct that is highly specific for RIG-I which would increase the load of perforin and granzyme B in NK cells and cytotoxic T cells thereby overcoming one of the obstacles of adoptive cell transfer of NK cells and $CD8^+$ T cells.

RIG I is also known to play a role in the viability and length of viability in stem cells. It is believed that activation of RIG I down regulates the processes which lead to early stem cell death. There is a need in the art for a RIG I agonist which will improve the viability and increase the engraftment potential of stem cells.

There are no known RIG I agonists which do not also stimulate an interferon response. Such response is undesired due the to accompanying inflammatory response.

There remains a need in the art for an improved oncolytic viral cancer therapy.

OBJECT OF THE INVENTION

It is an object of the invention to provide an RNA molecule which increases the amount of perforin in a cytotoxic cell.

It is an object of the invention to provide an RNA molecule which increases the amount of granzyme B in a cytotoxic cell.

It is an object of the invention to increase the amount of perforin in a cytoxic cell by administering a small molecule.

It is an objective of the invention to administer an RNA molecule to a cell including a cytotoxic cell and/or stem cell in an ex vivo process (i.e., while the autologous or allogeneic cell is outside the body), for the enhancement of adoptive cell therapies, including chimeric antigen receptor (CAR) technologies.

It is an objective of the invention to administer an RNA molecule to an indigenous cell including a cytotoxic cell and/or stem cell through an in vivo process (i.e., while the cell remains in the body).

It is an object of the invention to increase the amount of granzyme B in a cytotoxic cell by administering a small molecule.

It is an object of the invention to improve the ability to transfect stem cells.

It is an objective of the invention to extend the viability and engraftment rate of stem cells by administering an RNA molecule which binds RIG I.

It is an objective of the invention to increase the viability of a cytotoxic cell when exposed to virus during the ex vivo transfection process.

It is an objective of the invention to increase the viability of a cytotoxic cell when exposed to virus in vivo.

It is an objective of the invention to increase the serial killing capacity of a cytotoxic cell.

It is an object of the invention to treat viral infections, including chronic viral infections.

It is an object of the invention to treat cancer.

It is an object of the invention to treat liver cancer.

It is an object of the invention to treat multiple myeloma.

It is an object of the invention to treat Hepatitis C.

It is an object of the invention to treat HIV.

It is an object of the invention to clear cells acting as viral reservoirs.

It is an objective of the invention to administer a small RNA molecule to increase granzyme B and perforin in cell-line NK-92.

It is an objective of the invention to administer a small RNA molecule to increase Granzyme B and perforin in cell-line TALL-104.

It is an objective of the invention to administer a small RNA molecule to increase granzyme B and perforin in primary human cytotoxic lymphocytes such as natural killer cells and T cells.

It is an object to stimulate the RIG I pathway without upregulating interferon.

It is an object of the invention to extend survival time in a mammal having cancer using extracellular vesicles isolated from RIG I agonist A treated HEK 293 cells or NK cells.

It is an object of the invention to administer the novel RNA RIG I agonist in vivo or in vitro by coding it into RNA viral vectors or using oncolytic RNA viruses.

It is an object of the invention to administer the novel RNA RIG I agonist synergistically with Bispecific Killer cell Engager ("BIKEs"), Trispecific Killer cell Engager ("TRIKEs") and monoclonal antibodies to boost activation of the cell.

It is an object of the invention to increase immune response in the tumor microenvironment by delivering the RIG I Agonist A using targeted nanoparticles, liposomes, oncolytic viruses, viral vectors, monoclonal antibodies or ferrying and/or cell penetrating peptides.

It is an object of the invention to combine the Rig I agonists of the present invention with checkpoint inhibitors such as Anti-KIR antibodies, Anti-TIGIT, Anti-TIM3, Anti-PD1, Anti-PDL-1, and/or Anti-CTLA4.

It is an object of the invention to use the Rig I agonists of the present invention to understand the anergy of the effector cells as a diagnostic tool.

BRIEF DESCRIPTION OF THE INVENTION

We created an RNA construct comprising 56 RNA subunits identified herein as "Rig I agonist A" ("RIAA"). RIAA is highly specific for RIG I and increases the load of perforin and granzyme B in cytotoxic cells. This increases the viability, killing power and efficacy of cytotoxic cells and overcomes various obstacles of adoptive cell transfer of NK cells, CD8 T-cells and stem cells. RIAA is also the only RIG I Agonist known to the inventors which does not stimulate production of interferon.

RIAA is a small RNA molecule that can be used to transfect cells, including NK cells, CD8 T-cells and stem cells in vitro prior to administering the cells to a patient. The cells may be autologous or allogeneic. RIAA can also be administered in vivo to treat a patient's endogenous cells. Moreover, RIAA can be administered to a patient as a therapeutic small molecule without the need for in vitro processing of adoptive cells, moreover RIAA can be administered as monotherapy and/or combination therapy.

Applications of the present invention include the adult and pediatric treatment of solid tumors and hematological cancers including but not limited to malignant melanoma, ovarian cancer, bladder cancer, urothelial cancers, liver cancers, cervical cancer, head and neck cancers, EGFR+ tumors, HER1+ tumors, HER2+ tumors, pancreatic cancer, squamous cell carcinomas, sarcomas, non-small-cell lung cancer, merkel cell carcinoma, myelodysplastic syndromes, acute myeloid leukemia, acute lymphoblastic leukemia, glioblastoma multiforme, diffuse large B-cell lymphoma, mantle cell lymphoma, plasma cell leukemia, non-Hodgkin lymphoma, CD-20 positive B-cell malignancies, chronic myeloid leukemia, chronic lymphocytic leukemia, multiple myeloma and liver, chronic viruses and/or infections including but not limited to Hepatitis C and HIV, post-transplant lymphoproliferative disease and any therapy using stem cells.

DETAILED DESCRIPTION OF THE INVENTION

We have found a new family of RNA Rig I agonists which are useful in improving the transfection of NK cells and stem cells. These agonists comprise a single strand of RNA which binds to itself creating secondary structures which include a hairpin and a loop. We have discovered that the distance along the molecule between the hairpin and the loop ("the binding region") is critical for RIG I binding and activation.

Within the binding region, the distance between the hairpin and the loop should be between 7-80 bases. Below 7 bases it is believe that the structure cannot fold to fit in the binding groove on RIG I. If the binding region is over 80 bases, while the molecule may fold and fit into the RIG I binding site, it is believed that such a large molecule will in fact lessen activation of RIG I. The binding region between the hairpin and the loop needs to include a GC complementary base pair within 2-5 bases distance of each side of the loop to stabilize the loop structure. Additionally, the presence of at least one AU complementary pair in the loop area facilitates formation of the loop.

Representative of this family of small RNA molecules is the novel RNA construct identified as RIAA (SEQ ID NO: 1). RIAA is highly specific for RIG I that leads to a greatly increased load of perforin and granzyme B in NK cells and cytotoxic T cells. RIAA surprisingly does not induce an interferon response.

RIAA is a small RNA molecule that can be used to transfect cells, including NK cells, CD8 T-cells and stem cells in vitro prior to administering the cells to a patient. The cells may be autologous or allogeneic. RIAA can also be administered in vivo to treat endogenous cells in vivo. Moreover, RIAA can be administered to a patient as a small molecule therapeutic without the need for in vitro processing of adoptive cells.

Cytotoxic cells activated using the constructs and method of the present invention are useful in any application in which a cytotoxic cell with enhanced killing function is desired. Applications of the present invention include treatment of any cancer, including but not limited to multiple myeloma and liver, as well as viral infections including but not limited to chronic viral infections such as Hepatitis C and HIV.

Example 1: Ex Vivo Use of Rig I Agonists to Enhance Cells

Materials and Methods
Cell Culture

The human natural killer cell line NK-92 was purchased from American Type Culture Collection (ATCC) (ATCC, Manassas, VA, cat #: CRL-2407™). Cells were initially thawed in stem cell medium (CellGro; CellGenix, Freiburg, Germany) with 20% heat inactivated FBS (Invitrogen, Carlsbad, CA) and 1000 U/ml Proleukin (Novartis, Basel, Switzerland).

The human T cell line TALL 104 was purchased from American Type Culture Collection (ATCC) (ATCC, Manassas, VA, cat #: CRL-2407™). Cells were initially thawed in IMDM with 20% heat inactivated FBS (Invitrogen, Carlsbad, CA) and 1000 U/ml Proleukin (Novartis, Basel, Switzerland).

To evaluate NK cell activity, the human erythroblast cell line from a chronic myelogenous leukemia patient K562 (LGC Promochem/ATCC, Manassas, VA) was used as a target in 51-Chromium release and degranulation assays. K562 cells were cultured with RPMI, GlutaMAX 1640 (Invitrogen) and supplemented with 10% FBS.

Cells were incubated at 37° C. and 5% $CO_2$ with a humidity of 95% and cell numbers were determined every second day by Trypan Blue staining and Countess cell counter (Invitrogen).

NK-92 cells were cultured at a cell density of $0.5-1 \times 10^6$ cells/ml and daily supplemented with IL-2.

All cell culture has been conducted in a BSL2 environment under strict antibiotic free conditions.

TALL-104 cell line has been used at a cell density of $0.05-0.1 \times 10^6$ cells/ml in Iscove's Modified Dulbecco's Medium ("IMDM") supplemented with 10% fetal calf serum ("FCS"). The cells were supplemented with recombinant 500 U/ml IL-2.

RNA Constructs

Figure 5:
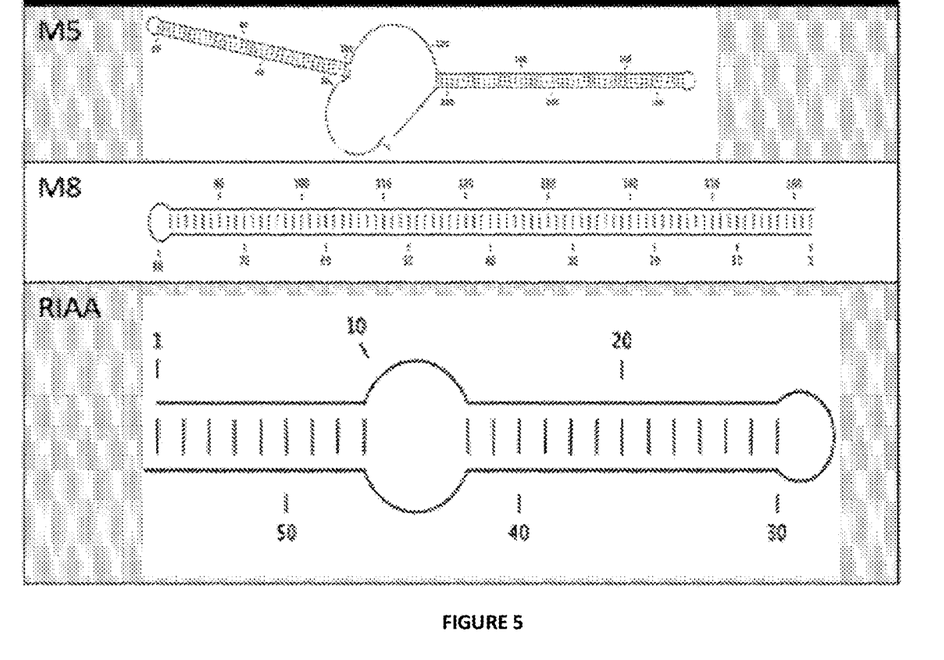
FIG. 5 is schematic overview of secondary RNA structure of RIAA compared with known RIG I stimulating agents, M5 and M8.

Previously reported RIG-I agonists (M5 and M8) were kindly shared by John Hiscott (Istituto Pasteur-Fondazione Cenci Bolognetti, Rome, Italy). Unfortunately, the M5 SEQ ID NO 2) and M8 (SEQ ID NO 3) compositions transferred were highly contaminated making it uncertain whether the activity came from the M5 or M8 molecules or whether the activity came from an unknown contaminant. (The M5 and M8 molecules are believed to be described in PCT publication WO/2016/011324). Therefore, the Rig I agonist A, M5 and M8 constructs were synthesized and Rig I agonist A), purified and quality controlled (by Dharmacon (GE Healthcare). M5, M8 and RIAA are shown in FIG. 5.

RIAA Sequence ID NO 1:
GACGAAGACCACAAACCAGAUAAAAAUAAUUUUUA

UCUGGUUGUUUGUCUUCGUC

M5 Sequence ID NO 2:
GACGAAGACCACAAACCAGATAAAAAATAATTTTTTATCTGGTTT

TGTGGTCTTCGTCC

M8 Sequence ID NO. 3
GACGAAGACCACAAACCAGATAAAAAAAAAAAAAAAAAAAAAAAA

ATAATTTTTTTTTTTTTTTTTTTTTTTATCTGGTTTTGTGGTCTTC

GTC

Transfection of HEK293 Cell Line with RIG-I Agonist

Human embryonic kidney cell line 293 (HEK 293) is a cell line that is well known in the art. Transfection was performed on newly trypsinized cells in suspension in 12-well plates, using approximately $2 \times 10^5$ cells/well in 1 ml IMDM/well for HEK293. For each transfection, and 1 µl Lipofectamine 2000 (Invitrogen) and 50 ng mRNA were used. The mRNA and the Lipofectamine 2000 were incubated for 30 min in 100 µl OPTI-MEM brand minimal essential medium (Gibco) before being added to the cell suspensions. The cell and Lipofectamine 2000-mRNA complex mix were immediately divided into 96-well plates, at $5 \times 10^3$ cells/well for HEK293 and incubated at 37° C. for 5 h before an extra 50 µl/well IMDM was added. After transfection, cells were pooled into a T-150 flask in OPTI-MEM. Supernatants were collected at 16, 24, 40, 48 hours and frozen for exosomal purification in −20 C.

Cultivation and Transfection of BMMSC with RIG-I Agonist

Transfection was performed as described above. Briefly, Bone Marrow Mesenchymal Stromal cells ("BMMSC") were acquired from three healthy donors. Ficoll separated bone marrow was plated in 6-well plates in 2 ml of Alpha-MEM (Invitrogen). The cells were then incubated at 37° C. in a 5% CO2 incubator for 5 days. After confirming the appearance of spindle-shaped cells on Day 3 in phase-contrast microscopy, and confluency of 70-90%, cells were washed with PBS twice, and digested with 2.5 mL of 0.25% GMP grade TrypLE Select CTS (ThermoFisher, Waltham, MA) for 2 minutes at 37° C., then neutralised with 7.5 mL complete minimal essential medium alpha ("α-MEM medium"). Thereafter $1 \times 10^6$ cells were used for confirming the following phenotype using flow cytometry: CD44, CD73, CD90, CD105, CD106, CD146, SSEA-1 and SSEA-4, while confirming these cells were negative for CD31, CD34, CD45, CD80, CD86 and HLA-DR. the panel is described in Table 1 below. The remaining cells were passaged every other day and transfected during passages 5-7. The cells were then seeded in 6-well plates at $5 \times 10^5$ cells/well for transfection. The transfection protocol was performed as described above. Cells were characterized 24 hours after transfection using flow cytometry and supernatant TGF-B levels were assessed by ELISA.

| | | Ab | Fluoro-chrome | Clone | Company | Cat no |
|---|---|---|---|---|---|---|
| | | | MSCs | | | |
| FL1 | FITC | CD105 | FITC | SN6/N1-3A1 | Ancell | 326-040 |
| FL2 | PE | CD166 | PE | 3A6 | BD | 559263 |
| FL3 | PE-Cy5 | CD90 | PE-Cy5 | 5E10 | BD | 555597 |
| FL4 | PE-Cy7 | CD73 | PE-Cy7 | AD2 | BD | 561258 |
| FL5 | APC | CD59 | APC | MEM-43 | Abcam | ab36467 |
| FL6 | APC-Cy7 | CD44 | APC-H7 | G44-26 | BD | 560532 |
| FL7 | Pacific Blue/V450 | CD31 | Pacific Blue | WM59 | BD | 561653 |
| | | CD45 | V450 | H130 | BD | 560367 |
| | | CD34 | Pacific Blue | 581 | BioLegend | 343512 |
| | | CD11b | V450 | ICRF44 | BD | 560480 |
| | | HLA-DR | V450 | L243 (G46-6) | BD | 642276 |
| FL8 | V500 | CD14 | V500 | M5E2 | BD | 561391 |
| FL11 | PE-Cy5.5 | CD79a | PerCP-Cy5.5 | HM47 | BD | 333153 |

Transfection of Hematopoietic Stem Cells ("HSCs")

Cord blood samples, collected from full-term normal deliveries (37-41 weeks), were diluted 1:1 with phosphate-buffered saline (PBS) (Gibco). Subsequently, mononuclear cells were isolated by centrifugation on Ficoll at 400 g for 40 mins. The mononuclear cells were collected, washed twice and resuspended in PBS with the addition of 0.5% human serum albumin ("HSA").

The $CD34^+$ fraction was isolated immunomagnetically using AutoMACS (Miltenyi Biotech) and the CD34 Direct Isolation Kit (Miltenyi Biotec) according to the manufacturer recommendations. In brief, after adding FcR Blocking Reagent, cells were labelled with MACS CD34 Microbeads for 30 min at 6-12° C. Subsequently, the labelled cells were enriched by passing the cell suspension through a column placed in a magnetic field. After the column removed from the magnetic field the positively selected cells were washed out from the column and collected. The purity of the CD34+ cell population was determined by flow cytometry immediately after isolation.

Cells were cultured in 25 cm² flasks at a cell density of $1 \times 10^5$/ml in a serum-free medium for hematopoietic stem and progenitor cells (CellGro SCGM, Cellgenix) supplemented with growth factors: stem cell factor (SCF) (20 ng/ml; PeproTech EC), thrombopoietin (TPO) (50 ng/ml; PeproTech EC) and fetal liver tyrosine kinase-3 ligand Flt-3 ligand (Flt-3L) (50 ng/ml; PeproTech EC). After 48 hours of incubation at 37° C. in a humidified atmosphere of 5% CO2, cells were resuspended at $1 \times 10^5$/ml in the CellGro SCGM medium supplemented with 20% HSA.

CD34-enriched cells were divided into aliquots of equal size (2-5 $10^5$ cells per aliquot) and were either not transfected, transfected without RNA(mock), or transfected with RIG-I agonist. By rinsing the transfection cuvettes two times with 1 ml IMDM, transfected cells were transferred into a 15-ml plastic tube and washed in a total volume of 10 ml of IMDM. Pelleted cells were incubated for 15 min in a humidified atmosphere at 37° C. and 5% CO2, then they were resuspended in 1 ml of Myleocult H5100 medium (Stem Cell Technologies Inc, Vancouver, Canada) supplemented with early-acting cytokines (fetal liver tyrosine kinase-3 ligand [FLT3L], stem cell factor [SCF], thrombopoietin [TPO], each at 10 ng/ml final concentration [all PeproTech, Inc., Rocky Hill, NJ]). Cells were cultured at a density of $1 \times 10^5$ cells/ml, in the presence of the general caspase inhibitor Z-V AD-FMK (BD Biosciences, Heidelberg, Germany) in a humidified atmosphere at 37° C. and 5% CO2.

We used the transfection instructions from Lonza, the manufacturer, (http://bio.lonza.com/fileadmin/groups/marketing/Downloads/Protocols/Generated/Optimized_Protocol_71.pdf), used the nucleofection program U08, and used more than $5 \times 10^5$ CD34-enriched cells. The RNA was transfected as described above. Cells were then characterized by detailed flow cytometry using the panel in Table 2.

TABLE 2

| | | Ab | | Fluoro-chrome | Clone | Company | Cat. No: |
|---|---|---|---|---|---|---|---|
| | | | HSCs | | | | |
| FL1 | FITC | CD90 (Thy1) | 6 | FITC | 5E10 | BD | 555595 |
| FL2 | PE | CD133 | 6 | PE | AC133 | Miltenyi | 130-080-801 |
| FL3 | PE-Cy5 | CD106 (VCAM-1) | 6 | PE-Cy5 | 51-10C9 | BD | 551148 |
| FL4 | PE-Cy7 | CD117 (c-kit) | | PE-Cy7 | 104D2 | BD | 339217 |
| FL5 | APC | CD135 | 6 | APC | BV10A4H2 | eBioscience | 17-1357-42 |
| FL6 | APC-Cy7 | CD34 | | APC-Cy7 | 581 | BioLegend | 343514 |
| FL7 | Pacific Blue/V450 | CD127 (IL7R) | 4 | Pacific Blue | A019D5 (PB) | BioLegend | 351306 |
| FL8 | V500 | CD45RA | 3 | V500 | HI100 | BD | 561640 |
| FL9 | Qdot605 | CD38 | | Qdot605 | HIT2 | Invitrogen | Q10053 |
| FL10 | PE-TxRed | Lineage Cocktail: CD3 CD14 CD16 CD19 CD41a | 20 + 10 | "biotin" | — UCHT1 M5E2 3G8 HIB19 HIP8 | BD | 51-9005225 and 551487 |

TABLE 2-continued

| | | HSCs | | | | |
|---|---|---|---|---|---|---|
| | | Ab | Fluoro-chrome | Clone | Company | Cat. No: |
| | | CD56 Glycophorin A Streptavidin PE-Texas Red | | B159 GA-R2 | | |
| FL11 | PE-Cy5.5 | CD123 (IL3RA) | 5 PerCP-Cy5.5 | 7G3 | BD | 558714 |

Construction of RNA Nanoparticles and Extracellular Vesicles

The nanoparticles were synthesized from RNA fragments (Trilink) according to a previously reported protocol (Shu et al., 2011). The RNA nanoparticles contained 2-F U and C nucleotides to render them resistant to RNase degradation in vivo. The RNA complex was then assembled by mixing the individual strands in stoichiometric ratio at room temperature ("RT") in PBS buffer.

NK92 or HEK 293 derived exosomes at a total protein concentration of 12 ug (measured by Bradford Assay) and 16 ug of RNA were mixed in 400 ul of electroporation buffer (1.15 mM potassium phosphate pH 7.2, 25 mM potassium chloride, 21% Optiprep) and electroporated in a 4 mm cuvette. For in vivo experiments, electroporation was performed in 400 μl and pooled thereafter.

Exosomes were generated using 50 ml conditioned medium (NK-cells S72 in OptiMem for 48 h) was spun at 300 g for 5 min to get rid of cell debris, filtered through 0.2 μm sterile filter and then ultracentrifuged at 110 000 g for 90 min. The pellet was re-suspended in PBS, total volume 300 μl. See, Liguni et al., JI 2012, Immune Surveillance Properties of Human NK Cell-Derived Exosomes.

Mice

Female and male C57BL/KaLwRij mice were purchased from Harlan CPB (Horst, The Netherlands) C57Bl/6, C57Bl/6 CD1$^{-/-}$, C57Bl/6 CD4$^{-/-}$, C57Bl/6 CD8$^{-/-}$, C57BL/6-Tg(ACTbEGFP)1Osb/J and Rag2$^{-/-}$ cy$^{-/-}$ mice were supplied by Microbiology and Tumor Biology Center, Karolinska Institutet. All animals were housed in our animal facilities at Clinical Research Centre at Huddinge University Hospital, Karolinska Institutet under conventional conditions including access to tap water and standard chow ad libitum. All mice were 8-10 weeks old at the beginning of each experiment. Experiments performed in this study were approved by the local ethical committee in South Stockholm, Sweden.

MM Cell Injection and Induction of Multiple Myeloma

Groups of C57BL/KaLwRij mice were injected i.v. with $10^5$ eGFP-5T33 MM and/or non-transduced 5T33 MM cells suspended in a total volume of 100 μl sterile PBS per mouse. Control mice were injected with equal volume of PBS i.v. The animals were examined twice daily for the development of paraplegia. At weekly intervals and at the time of disease development, the mice were euthanized by $CO_2$ inhalation and the spleens, livers, thymus and lymph nodes were excised and kept in PBS until processing for preparation of single-cell suspensions. Bone marrow from femora and tibiae were obtained by flushing PBS into the cavity of bones.

Irradiation and Inoculation of Tumor Cells

Tumor cells were washed three times with PBS and gamma-irradiated with 60 Gy in a $^{137}$Cs Gammacell 2000 device (Molsgaard Medical, Horsholm, Denmark). Immediately after irradiation, they were injected subcutaneously or cultured for further in vitro analysis. C57Bl/6 and C57Bl/KaLwRij were immunized following standard protocols. Briefly, prior to injection, tumor cells were washed, counted and resuspended in PBS (0.2 ml) at their final concentrations. A 1 cc tuberculin syringe with a 27-gauge needle was used to inject tumor cells three times, in three-week intervals, and mice were also checked for tumor presence twice a week.

Preparation of Effector Cells

Suspensions of spleen single cells from mice were pooled in serum-free RPMI-1640 medium by filtering the suspension through mesh with the aid of a homogenizer to exert gentle pressure on the spleen fragments. Erythrocytes were lysed in ammonium chloride solution [0.15 mol/L NH4Cl, 10 mmol/L KHCO3, 0.1 mmol/L edetic acid (EDTA), pH 7.2]. Obtained cells were washed twice with phosphate-buffered saline (PBS) and resuspended in the complete RPMI-1640 medium [RPMI-1640 medium supplemented with 10% inactivated FCS, 2 mmol/L L-glutamine, 25 mmol/L NaHCO3, 1 mmol/L sodium pyruvate, 25 mmol/L N-2-hydroxyethylpiperazine-N'-2-ethanesulfonic acid (HEPES), 100 kU/L penicillin G, and 100 mg/L streptomycin] with Trace Elements A (Mediatech inc., Herndon, VA). Proleukin® (rIL-2) in fresh complete RPMI medium was added on day 0 and every other day onwards. Cells were cultured in a concentration of $1 \times 10^6$ cells/ml and cell density was determined daily.

Ex Vivo Separation of Effector Cells

After single-cell suspension, mouse cells were separated using a CD8 Mouse Microbeads Kit (Miltenyi Biotech, Bergisch Gladbach, Germany) according to the manufacturer's instructions. Briefly, single cell suspensions from different organs were prepared as described above and the cell number was determined. After cell centrifugation at 300 g for 10 minutes, the supernatant was removed completely. The cell pellet was resuspended in 90 μl of rinsing buffer (PBS, 0.5% BSA, 2 mM EDTA). Cells were mixed with 100 of CD8 microbeads per $10^7$ total cells and incubated for 15 minutes at 4° C. Prior to magnetic separation, cells were washed with 2 ml of rinsing buffer per $10^7$ cells, centrifuged at 300 g for 10 minutes to remove supernatant and resuspended in 500 μl of rinsing buffer. Meanwhile, the magnetic columns were placed in the magnetic field of a suitable MACS separator and prepared for sorting, by rinsing with 3 ml of rinsing buffer. Finally, the cell suspension was applied into the column, which was rinsed three times with 3 ml of rinsing buffer. All the unlabeled (negative) cells were rinsed out and collected into a 15 ml falcon tube. In order to collect the labeled effector cells, the column was removed from the magnetic field, 5 ml of rinsing buffer was applied on the column and the plunger was used to flush out the positive cell fraction into a clean 15 ml falcon tube.

The negative fraction was stimulated in vitro at a 1:1 effector:target (E:T) ratio with 50 units/ml IL-2 in a 24-well plate (BD) After 5 days of in vitro stimulation, cells were harvested and used in $^{51}$Cr-release assays.

Degranulation and Cytotoxicity Assay

To analyze NK cell ability to degranulate, cells were cultured at a density of a $1 \times 10^6$ cells/ml in a 96 well plate and incubate alone or with K562 at a ratio of 1:1 or with PMA&Iono (0.5 µg/ml, company, where) for 4-6 hours. Following one hour of incubation, Golgi Stop (BD) was added to cultures to inhibit protein transportation. Subsequently, cells were stained for CD56 and CD107a for 30 minutes at 4° C.

The cytotoxic function was measured in an 18 hour $^{51}$Cr-release assay in triplicates. Briefly, $1 \times 10^6$ target cells were labeled with 100 µl $^{51}$Cr (specific activity of 1 mCi/ml) and were incubated for one hour at 37° C. 5T33 and LPS Blasts were used as targets. CTL cells were co-incubated with target cell serial dilutions prepared in triplicates, with a maximum E:T ratio of 100:1. RPMI medium was used as negative control and for positive control cells were incubated with 1% of Triton X. After incubation in a V-bottom shaped 96-well plate for 18 hours at 37° C., 70 µl of supernatant were aspirated from each well and counted using a Packard Cobra Auto-Gamma 5000 Series Counting system (Meriden, CT, USA). The percentage of the spontaneous release was calculated from the following formula: % specific $^{51}$Cr release=(sample release−spontaneous release)/(maximum release−spontaneous release)×100.

In Vivo Depletion of Mouse CD4$^+$ and CD8$^+$ Cells

C57Bl/6 mice were tumor challenged by inoculating them with $10^6$ 5T33 MM cells via the tail vein or subcutaneously. To deplete CD4 cells in vivo, mice were injected starting 2 days before immunization with 200 µg i.p. of anti-CD4 mAb, and every 5 days thereafter, until termination of the experiment, with 200 µg i.p. of the anti-CD4 mAb. Control mice were injected with a similar volume (0.2 ml) and dose of mouse IgG antibody (Sigma) as an isotype control. The efficacy of depletion of CD4$^+$ cells was monitored by flow cytometric analysis of spleen cells at the endpoint. Animals exhibiting >1.0% CD4$^+$ cells in the spleen were excluded from the study (n=2).

In parallel, in vivo depletion of CTLs was carried out using purified anti-CD8 MAbs (Clone 2.43); 0.5 mg per mouse of antibody was injected intraperitoneally every five days from day −2, when depleting during the establishment of tumor, until the endpoint.

Mice were monitored for development of paraplegia or subcutaneous tumor and their survival kinetics were compared.

Flow Cytometry

Phenotyping was analyzed with fluorochrome-conjugated antibodies against CD2 (RPA-2.10), CD11b (ICRF44) CD57 (NK-1) DNAM1 (DX11), NKp44 (p44-8.1) NKp46 (9E2), NKp30 (p30-15), CD107a (H4A3), NKG2D (1D11) (BD, Franklin Lakes, NJ); NKG2C (134591) (R&D Systems, Abingdon, United Kingdom); CD56 (HCD56), NKp80 (5d12), CD161 (HP-3G10), CD319 (162.1), CD352 (NT-7), (Biolegend, San Diego, CA); CD244 (C1.7) (Beckman Coulter, Brea, CA); Siglec 7 (REA214) (Miltenyi, Bergisch Gladbach, Germany) and handled according to the manufactory procedure. For intracellular staining of Perforin (dG9), Granzyme B (GB11) (BD), cells were washed with PBS followed by fixation and permeabilization with Cytofix/Cytoperm (BD) and incubated for 20 minutes at +4° C. Following fixation and permeabilization, cells were washed and stained in Permwash according to manufactory protocol.

All cells were acquired by either a Partec Cyflow ML or BD LSR Fortessa flow cytometer (BD) and analyzed using FlowJo software (FlowJo LLC, Ashland, OR).

Statistics

The non-parametrical Kruskal Wallis test was used to compare absolute cell counts, NK cell percentages and cytotoxicity of all cultures. Log rank test was performed using GraphPad Prism version 6 for MacOSX (Graph Pad Software, San Diego, California, USA) to analyze statistical significance (p<0.05) of the survival curves.

Results

Perforin and Granzyme B Content

Figure 1:
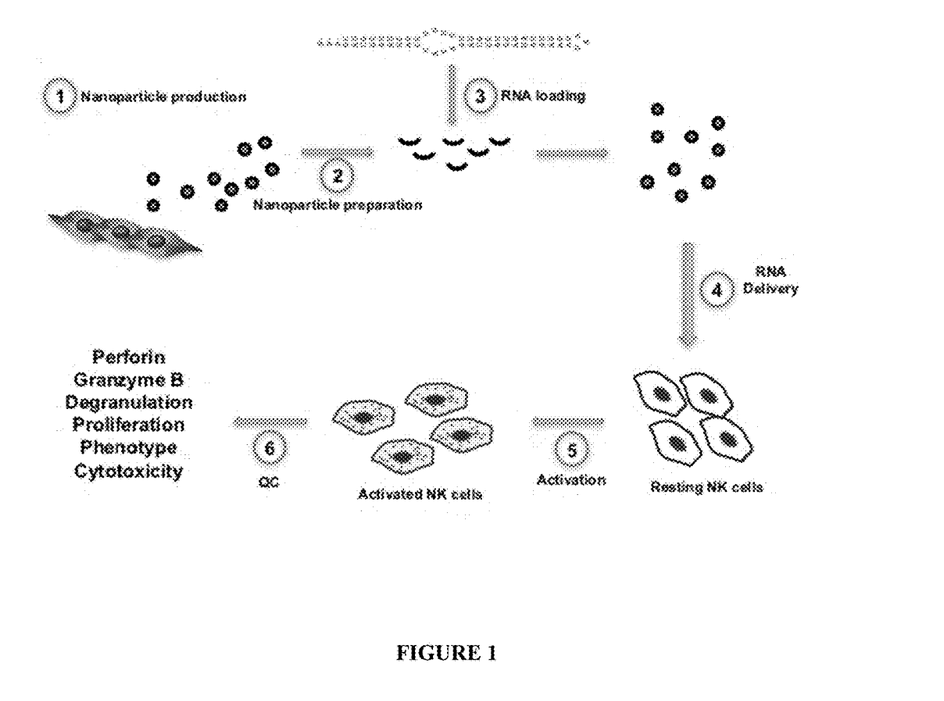
FIG. 1 is a schematic drawing of the experimental protocol.
Figure 2:
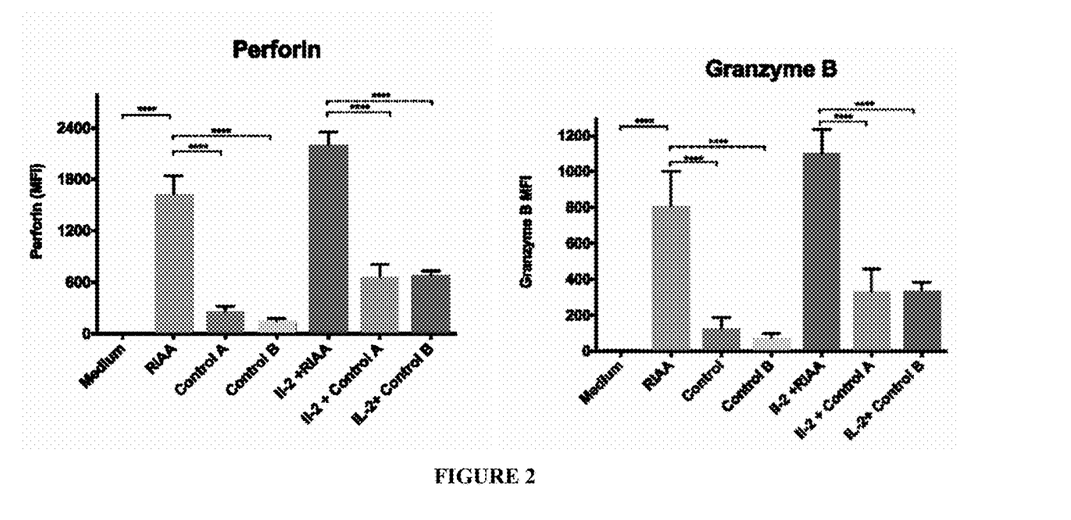
FIG. 2 is a pair of bar graphs showing the increase of perforin and granzyme B load of NK cells following administration of Rig I agonist A.

Four hours after transfection of three batches of NK cells treated separately with RIAA, M5 or M8, we analysed the granzyme B and perforin load of the NK cells using flow cytometry as described above. In IL2 stimulated NK cells that were treated with RIAA, we saw a 1600-2000 fold increase in perforin content and a 800-1100 fold increase in granzyme B content when compared to the IL2 stimulated M5 and M8 controls (FIG. 2). M5 showed a 141-921 fold increase in perforin content over untreated cells and M8 showed a 110-783 fold increase in perforin content over untreated cells. M5 showed a 70-460 fold increase in granzyme B content over untreated cells and M8 showed a 55-391fold increase in perforin content over untreated cells. The data in FIG. 2 is further shown in tables 3 and 4 below.

TABLE 3

| NK92: | Perforin | |
|---|---|---|
| | Median | Range |
| M5 | 254.7 | (141-380) |
| M8 | 146 | (110-206) |
| IL2 + M5 | 659 | (402-921) |
| IL2 + M8 | 677 | (612-783) |
| RIAA: | 1620 | (1210-1966) |
| IL2 + RIAA: | 2199 | (1900-2260) |
| iL2: | 589 | (522-675) |

TABLE 4

| NK92: | Granzyme B | |
|---|---|---|
| | Median | Range |
| M5 | 127.3 | (70-190) |
| M8 | 73 | (55-103) |
| IL2 + M5 | 329.3 | (201-460) |
| IL2 + M8 | 338.3 | (306-391) |
| RIAA: | 809.7 | (605-983) |
| IL2 + RIAA: | 1099 | (950-1218) |
| IL2: | 294.3 | (261-337) |

Figure 9:
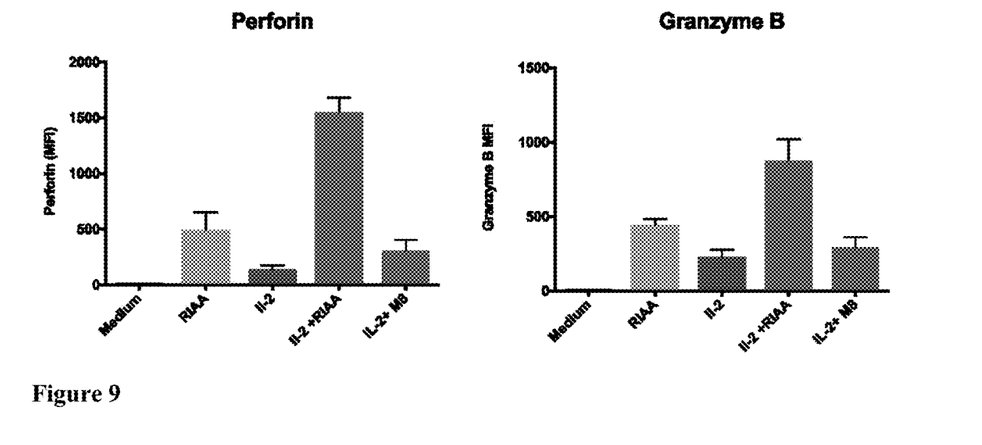
FIG. 9 is a bar graph showing the increase of Perforin and Granzyme B in T cells using RIG I agonist A treatment.

Two, four and six hours after transfection of TALL-104 cell line with either RIAA and M8, Granzyme B and Perforin load of this gamma-delta T cell line was assessed using the same panel described above. We have observed, in a similar fashion and the upregulation of granzyme B and perforin (FIG. 9) in the arms treated with RIAA. Cells treated with RIAA showed an increase in perforin from 270-1722. M8 showed a 190-381 fold increase in perforin content over untreated cells. M8 showed a 224-365 fold increase in perforin content over untreated cells. This data is also shown in Tables 5 and 6 below.

TABLE 5

| | Perforin | |
| TALL: | Median | Range |
| --- | --- | --- |
| RIAA | 489.7 | (270-701) |
| IL2 + RIAA: | 1549 | (1288-1722) |
| IL2: | 138 | (114-180) |
| IL2 + M8: | 303.3 | (190-381) |

TABLE 6

| | Granzyme B | |
| TALL | Median | Range |
| --- | --- | --- |
| RIAA | 443 | (405-483) |
| IL2 + RIAA: | 876 | (730-1018) |
| IL2: | 227.3 | (180-281) |
| IL2 + M8: | 289.7 | (224-365) |

Serial Cytotoxicity Assay

Figure 3:
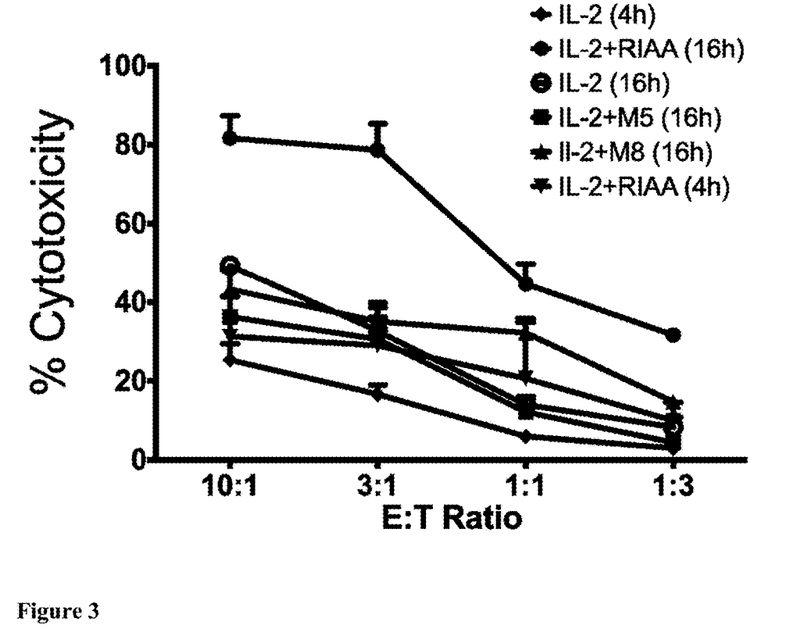
FIG. 3 is a line graph showing the serial cytotoxic capacity of NK cells after stimulation with RIAA.
Figure 4:
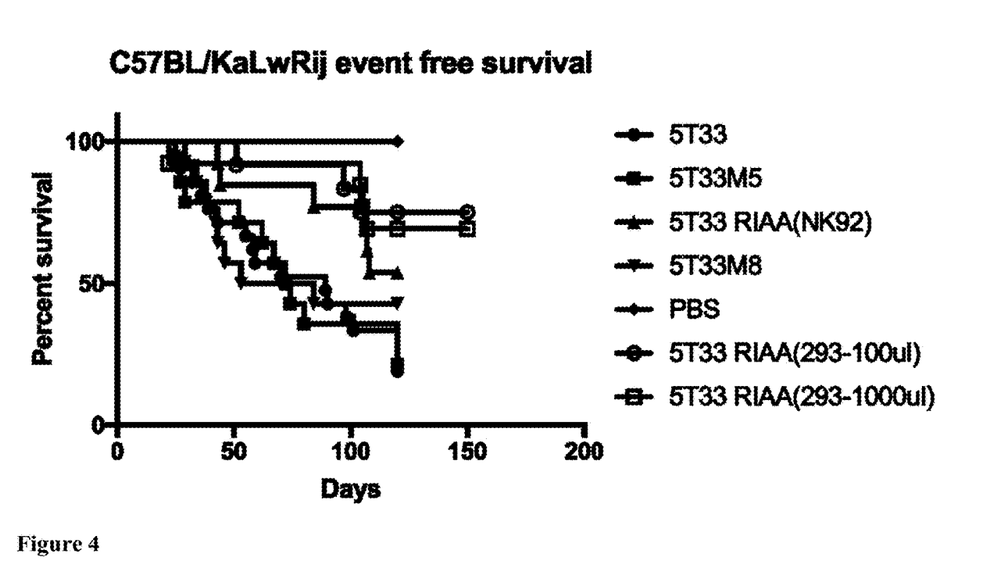
FIG. 4 is a line graph showing subcutaneous administration of RIAA and other RIG I agonists into syngeneic immunocompetent tumor bearing mice.

Serial cytotoxic capacity of NK cells against K562 targets were performed as previously described (Bhat et al., 2007). M5, and M8 agonists as well as RIAA ferrying nanoparticles were transfected on IL-2 activated NK cells with an overnight incubation. A cytotoxicity assay was performed thereafter. M5 and M8 transfected NK cells had no significant difference in serial killing capacity. However, RIAA transfected cells had a significant increase in serial cytotoxic activity (FIGS. 3 and 4).

In Vivo Tumor Rejection Assay

The 5T33MM tumors were established as defined above. RNA ferrying nanoparticles were administered day 5 after tumor cell injection. The particles were injected 6 times (1 µg/g; 500 µL of PBS) every 2 h. Comparative tumor engraftment showed that RIAA particle administered mice had a delayed MM engraftment (FIG. 4). Further studies have shown that subcutaneous administration of HEK293 derived EVs delayed survival in a dose dependent manner (FIG. 9) in the same experimental model.

Discussion

In this study, we aimed to identify optimal inducers of perforin and granzyme B production in cytotoxic lymphocytes such as natural killer cells and cytotoxic T lymphocytes. In an attempt to induce a RIG-I dependent induction, we have initially tested the hypothesis of RIG-I induction leading to better perforin and granzyme B expression by using previously published RIG-I agonists (M5 and M8). Although we can also observe an increase in type I interferon secretion as previously reported, we have not observed a significant increase in either of the cytotoxic granules. In an effort to accommodate this, we have tested a new construct, much shorter and structurally different than the constructs previously defined. Introduction of this construct to natural killer cells and T cells using transfection or EV mediated delivery resulted in a significant and rapid increase in expression of perforin followed by granzyme B. To our knowledge, this is the first report of an RNA construct leading to such a drastic difference in the proteomic profile of cytotoxic lymphocytes.

We thereafter administered this RNA construct in to a previously reported syngeneic immunocompetent experimental multiple myeloma (MM) model in which we have shown that activated NK cells are critical for MM rejection in a dose dependent manner. In this case, there was no adoptive transfer of NK cells but merely RNA administration for a relatively brief period shortly after establishment of minimal residual disease. The construct resulted in a significant delay in tumor development compared to all other tested treatments. We believe that this phenomenon is likely due to an increase in serial cytotoxic capacity of the cells. We have not observed any off-target effects or severe adverse events. However, in vivo delivery of the RNA molecule was suboptimal and further studies are required to elucidate the best platform and method of delivery for optimal anti-tumor activity.

Stimulation and activation of the cytosolic RNA recognition receptors RIG-I and MDA-5 are very attractive to boost the immune response of the activated cells. The activating will stimulate the synthesis of a broad range of antiviral effectors, cytokines and chemokines that that have a crucial role for priming, expansion and polarization of immune cells (Beljanski et al., 2015). It has been previously shown that activating of RIG-I with 5'pppRNA leads to a solid expression of proinflammatory and antiviral genes (Chiang et al., 2015). As discussed elsewhere it seems that the length of the construct has a critical effect on the strength of the antiviral response, if the construct is between 59-nucleotides to 99-nucleotides the antiviral response was heightened compared to shorter constructs (Chiang et al., 2015). Additionally, a greatly increased serial killing of K562 was shown in vivo (FIGS. 2 and 3) and could also be confirmed in vitro with the tumor rejection assay (FIG. 4). This greatly increased cytotoxic activity is a direct effect of the boosted perforin and granzyme B levels.

Figure 6:
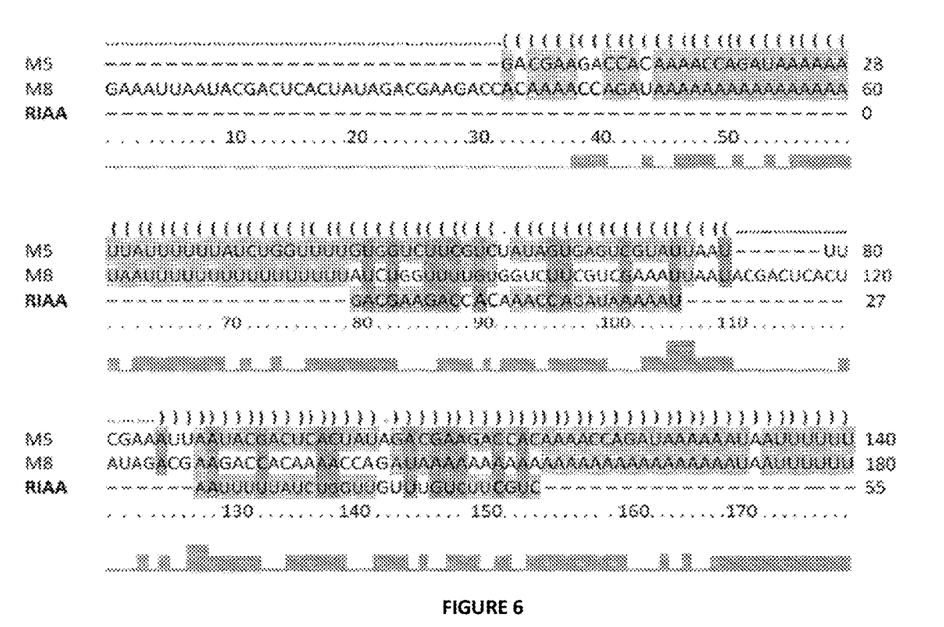
FIG. 6 is a sequence comparison of an M5 sequence (SEQ ID NO: 4), an M8 sequence (SEQ ID NO: 5), and a Rig I agonist A (SEQ ID NO.: 1).

The RNA sequence and secondary structure of RIAA differs entirely from the previously published RIG-I agonists M5 and M8. RIAA is significantly shorter than both of the other RNA molecules and shares no significant sequence homology (FIG. 6). M5 is a linear molecule with a hairpin on one side and M8 is a two-sided dsRNA strand with one hairpin. In contrast, the RIAA structure is one armed with a hairpin and a loop structure (FIG. 5). These structural differences are what account for the greatly increased activity of RIAA over other known RIG I agonists.

In summary, we have demonstrated that the RIAA RNA construct induces an increased perforin and granzyme B expression, which leads to higher serial selective cytotoxic capacity both in vitro and in vivo. Potential applications of this group of molecules can be a simple ex vivo treatment of cells before adoptive transfer or direct administration. Further studies to understand the safety and efficacy profile of these constructs are warranted.

Example 2: In Vivo Uses

The RNA constructs of the present invention can be administered to patients by either implanting/administering cells expressing the construct or as small molecules. Such cells or small molecules could be injected in the patient or administered via conventional routes. Cells receiving the RNA constructs would then increase production and storage of granzyme B and/or perforin to improve the serial killing ability of the cells.

The RNA constructs of the present invention can be administered via injection, oral, nasal or mucosal delivery using technologies known in the art. Potential therapeutic applications include cancer, liver gene therapy, single gene disorders, storage disorders as well as tumor retargeting genes.

Cancers treatable by the present invention include carcinomas, sarcomas, lymphomas, leukemias, and blastomas: acute lymphoblastic leukemia (all), acute myeloid leukemia, adrenocortical carcinoma, aids-related cancers, anal cancer, astrocytoma, basal-cell carcinoma, extrahepatic bile duct cancer (cholangiocarcinoma), bladder cancer, bone tumor (osteosarcoma/malignant fibrous hi stiocytoma), brainstem glioma, brain cancer, cerebral astrocytoma/malignant glioma, ependymoma, medulloblastoma, supratentorial primitive neuroectodermal tumors, visual pathway and hypothalamic glioma, breast cancer, bronchial adenomas/carcinoids, burkitt's lymphoma, central nervous system lymphoma, cervical cancer, chondrosarcoma, chronic lymphocytic leukemia, chronic myelogenous leukemia, chronic myeloproliferative disorders, colon cancer, cutaneous t-cell lymphoma, desmoplastic small round cell tumor, endometrial cancer, ependymoma, esophageal cancer, Ewing's sarcoma, intraocular melanoma, retinoblastoma, gallbladder cancer, gastric (stomach) cancer, gastrointestinal carcinoid tumor, gastrointestinal stromal tumor (gist), extracranial, extragonadal, or ovarian germ cell tumor, gestational trophoblastic tumor, glioma of the brain stem, childhood cerebral astrocytoma glioma, hairy cell leukemia, head and neck cancer, heart cancer, hepatocellular (liver) cancer, hodgkin lymphoma, intraocular melanoma, islet cell carcinoma (endocrine pancreas), kaposi sarcoma, kidney cancer (renal cell cancer), acute lymphoblastic leukaemia (also called acute lymphocytic leukemia), acute myeloid leukemia (also called acute myelogenous leukemia), chronic lymphocytic leukemia, chronic myelogenous leukemia (also called chronic myeloid leukemia), hairy cell leukemia, lip and oral cavity cancer, liposarcoma, non small cell lung cancer, small cell lung cancer, macroglobulinemia, waldenström, male breast cancer, malignant fibrous histiocytoma of bone/osteosarcoma, medulloblastoma, melanoma, intraocular (eye)melanoma, Merkel cell cancer, mesothelioma, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, chronic myelogenous leukemia, acute myeloid leukemia, myeloid leukemia, multiple myeloma (cancer of the bone-marrow), myeloproliferative disorders, myxoma, nasal cavity and paranasal sinus cancer, nasopharyngeal carcinoma, neuroblastoma, non-small cell lung cancer, oligodendroglioma, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer, paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma, salivary gland cancer, soft tissue sarcoma, uterine sarcoma, Sézary syndrome, melanoma and non-melanoma skin cancer, merkel cell skin carcinoma, small cell lung cancer, small intestine cancer, soft tissue sarcoma, squamous cell carcinoma, squamous neck cancer with occult primary, stomach cancer, supratentorial primitive neuroectodermal tumor, t-cell lymphoma (mycosis fungoides and sézary syndrome), testicular cancer, throat cancer, thymoma and thymic carcinoma, thyroid cancer, transitional cell cancer of the renal pelvis and ureter, trophoblastic tumor, ureter and renal pelvis transitional cell cancer, urethral cancer, uterine cancer, uterine sarcoma, vaginal cancer, visual pathway and hypothalamic glioma, vulvar cancer, Waldenström macroglobulinemia, Wilms tumor (kidney cancer).

The present invention is also useful in treating genetic disorders such as: 21-hydroxylase deficiency, achondroplasia, acute intermittent porphyria, adenylosuccinate lyase deficiency, Adrenoleukodystrophy, Alagille syndrome, Alexander disease, Alström syndrome, Amelogenesis imperfecta, biotinidase deficiency, CGD Chronic granulomatous disorder, Di George's syndrome, fanconi anemia, G6PD deficiency, lipoprotein lipase deficiency, Muscular dystrophy, Duchenne type, Siderius X-linked mental retardation syndrome caused by mutations in the PHF8 gene, X-linked severe combined immunodeficiency (X-SCID), X-linked sideroblastic anemia (XLSA).

Metabolic disoders treatable with the present invention include: Niemann-Pick disease, Tay-Sachs disease, Gaucher disease, Fabry disease.

Example 3: Uses in Viral Infection Settings Including Chronic Viral Infections

The enhanced killing ability of the Rig I agonist A transfected cells of the present invention will give it enhanced ability to clear infected cells having a high viral load. As such the present invention will permit clearing of viral reservoirs eliminating the ability of these infected cells to infect other cells or release their contents. The RNA constructs of the present invention can be administered to patients by either implanting/administering cells expressing the construct or as small molecules. Such cells or small molecules could be injected in the patient or administered via conventional routes. Cells receiving the RNA constructs would then increase production and storage of granzyme B and/or perforin to improve the serial killing ability of the cells.

Example 4 RIAA Uses in Stem Cells

The RNA constructs of the present invention can be used to extend the life of stem cells. RIG I is known to mediate DNA repair mechanisms in stem cells. The administration of the present invention is expected to enhance RIG I activity and therefore extend the viability of stem cells treated with the present invention.

In an ongoing experiment, cd90 bone marrow samples were obtained from 10 healthy human donors undergoing orthopedic surgeries. Each sample was diluted in Hanks' balanced saline solution (HBSS) and passed through a 70-μm cell filter.

Single cells suspensions were incubated with previously titrated antibody mix: CD105, CD90, CD73, CD44, CD31, CD45, CD34, CD11b, HLA-DR and CD14 (all from BD Biosciences) and incubated for 20 minutes at room temperature. After washing, the cells were re-suspended in FACS buffer at a concentration of 20×106/ml. Cells were sorted with an Aria III (BD Biosciences) equipped with 405, 488, 561 and 633 lasers. Cells were recovered and grown to confluence in DMEM, 20% FCS.

RIAA was transfected 24 h after seeding on MSCS after seeding them in flasks. They were produced by exosomes with the 293 system as defined.

The healing potential of mesenchymal stem cells ("MSC") in a wound model in vivo will be assessed. At passage 8, selected MSC lines with and without RIAA treatment will be loaded onto polyvinyl alcohol sponges and implanted into NOD/SCID immunodeficient mice as previously described (Deskins D L, Ardestani S, Young P P. The polyvinyl alcohol sponge model implantation. J Vis Exp. 2012; (62):3885.). Briefly, sponges will be hydrated and sterilized in saline solution. Three sponges per MSC cell line will be loaded with 7.5×106 cells in 25 µl of phosphate-buffered saline. Each mouse will be implanted with three sponges, each sponge containing a different MSC line. All sponges will be removed 21 days after implantation and cut in half before being preserved in 10% buffered formalin for 24 hours. After the formalin soak, the sponges will be embedded cut-side-down in paraffin and sectioned for staining.

Figure 7:
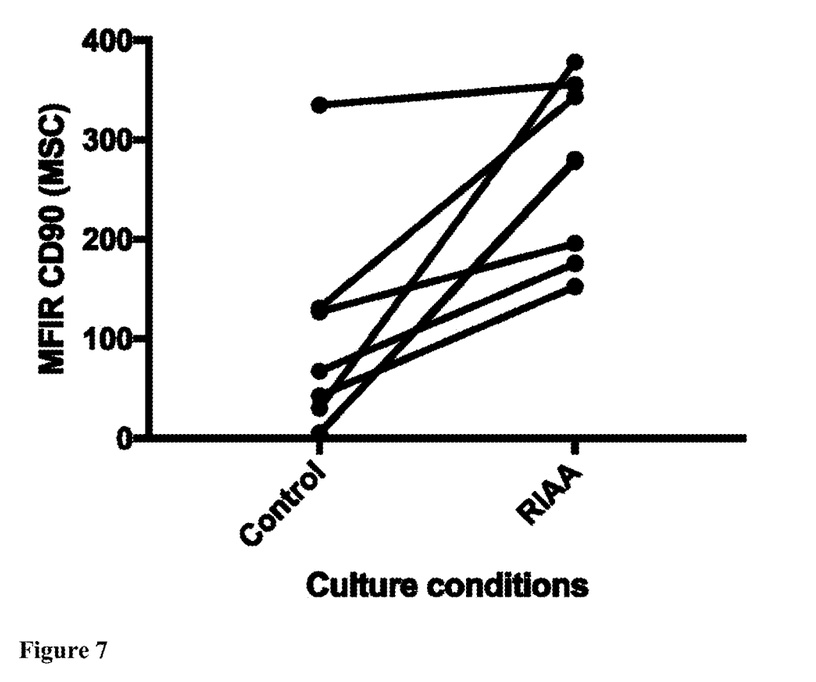
FIG. 7 is a line graph showing the changes in CD90 receptor density, per donor, in Mesenchymal Stromal Cells, with and without RIG I agonist A treatment.
Figure 8:
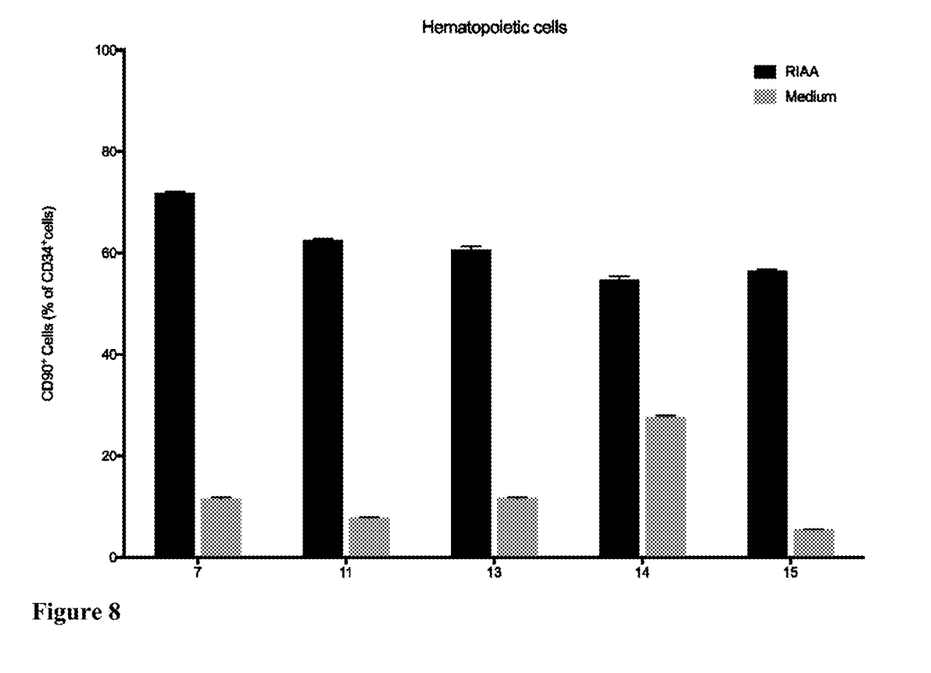
FIG. 8 is bar graph showing the increase in CD90 cells following administration of Rig I agonist A.

Referring to FIGS. 7 and 8, it is believed that the RIAA treated MSC lines will exhibit significantly greater growth than the controls. Upregulation of CD90 in these cells suggest a direct or surrogate role of the RIAA treated cells in tumor suppression (Ref 1). Abeysinghe HR, Cao Q, Xu J, Pollock S, Veyberman Y, Guckert N L, Keng P, Wang N (2003). "THY1 expression is associated with tumor suppression of human ovarian cancer". Cancer Genet. Cytogenet. 143 (2): 125-32. doi:10.1016/50165-4608(02)00855-5. PMID 12781446. Also of importance is the possibility of increased engraftment and adhesion of MSC and HSCs with RIAA stimulation as CD90 is clearly implicated in increased adhesion, extravasation and homing of cells. Rege T A, Hagood J S (2006). "Thy-1 as a regulator of cell-cell and cell-matrix interactions in axon regeneration, apoptosis, adhesion, migration, cancer, and fibrosis". FASEB J. 20 (8): 1045-54. doi:10.1096/fj.05-5460rev. PMID 16770003. Wetzel A, Chavakis T, Preissner K T, Sticherling M, Haustein U F, Anderegg U, Saalbach A (2004). "Human Thy-1 (CD90) on activated endothelial cells is a counterreceptor for the leukocyte integrin Mac-1 (CD11b/CD18)" (abstract page). J. Immunol. 172(6): 3850-9. doi:10.4049/jimmunol.172.6.3850. PMID 15004192.

Example 5. Adoptive Cell Transfer

In a most preferred use, a Rig I agonist is used to treat cells prior to adoptive cell transfer to a patient. Using the protocols described above RIAA can be used at any time during ex vivo manipulation. Preferred concentration of a Rig I agonist in culture ranges are from about 0.4 mM to about 10 mM. Most preferred is 0.5 mM to 6 mM These cells can thereby be immediately infused or frozen for a later infusion time point using protocols well known in the art. Rig I agonist administration can be done both in vivo and ex vivo as a single dose or repetitively using the dose window where serum concentration of the inhibitor can be between 0.4-6 uM, preferentially the lower dose. Such adoptive cell transfer can be used to treat the conditions described under Example 3 above.

Example 6. Treatment of Viral Inflammation

The present invention can also be used to treat patients suffering from inflammation caused by a viral infection such as myositis, myocarditis, viral arthritis, viral encephalitis and meningitis. In such diseases Rig I agonists can be co-administered with anti-viral therapy to reduce or stop the recognition of the virus by the immune system thereby reducing, preventing or eliminating inflammation. This could only be used with antiviral therapies that do not rely on or fully utilize immune responses. Such antivirals include: adamantane antivirals such as amandatind and rimantidine; antiviral boosters such as ritonavir and cobicistat; chemokine receptor antagonists such as maraviroc; integrase strand transfer inhibitors such as maraviroc, dolutegravir and elvitegravir; miscellaneous antivirals such as sofosbuvir, enfuvirtide, foscarnet and fomivirsen; neuraminidase inhibitors such as peramivir, oseltamivir and zanamivir; non-nucleoside reverse transcriptase inhibitors (NNRTIs) such as favirenz, nevirapine, delavirdine, etravirine and rilpivirine; NS5a inhibitors such as daclatasvir; nucleoside reverse transcriptase inhibitors (NRTIs) such as zidovudine, didanosine, stavudine, lamivudine, abacavir, emtricitabine and entecavir; protease inhibitors such as saquinavir, ritonavir, indinavir, nelfinavir, amprenavir, lopinavir, atazanavir, fosamprenavir, tipranavir and darunavir; and purine nucleosides such as ribavirin valacyclovir, famciclovir, acyclovir, ganciclovir, valganciclovir and cidofovir. Dosing instructions for these drugs alone and in combination are well known in the art.

Example 7: Increasing In Vivo Efficacy of RNA Viral Therapies

The Rig I agonists are also useful when administered in vivo to increase in vivo efficacy of RNA virus based oncolytic virus therapies such as vesicular stomatitis virus, poliovirus, reovirus, senecavirus, ECHO viruses such as Rigvir for indications such as bladder carcinoma, brain tumors, gynecological tumors, Hepatocellular carcinoma, melanoma, multiple myeloma, prostate carcinoma, soft tissue sarcoma and Solid tumors. The Rig I agonist would help inhibit intracellular antiviral defense mechanisms thus increase the efficacy of distribution of the oncolytic virus within the tumor. Target serum levels for in vivo administration of Rig I agonist are between 0.2 and 6 mM.

Example 8: Intracellular Cytokine Staining

Figure 10:
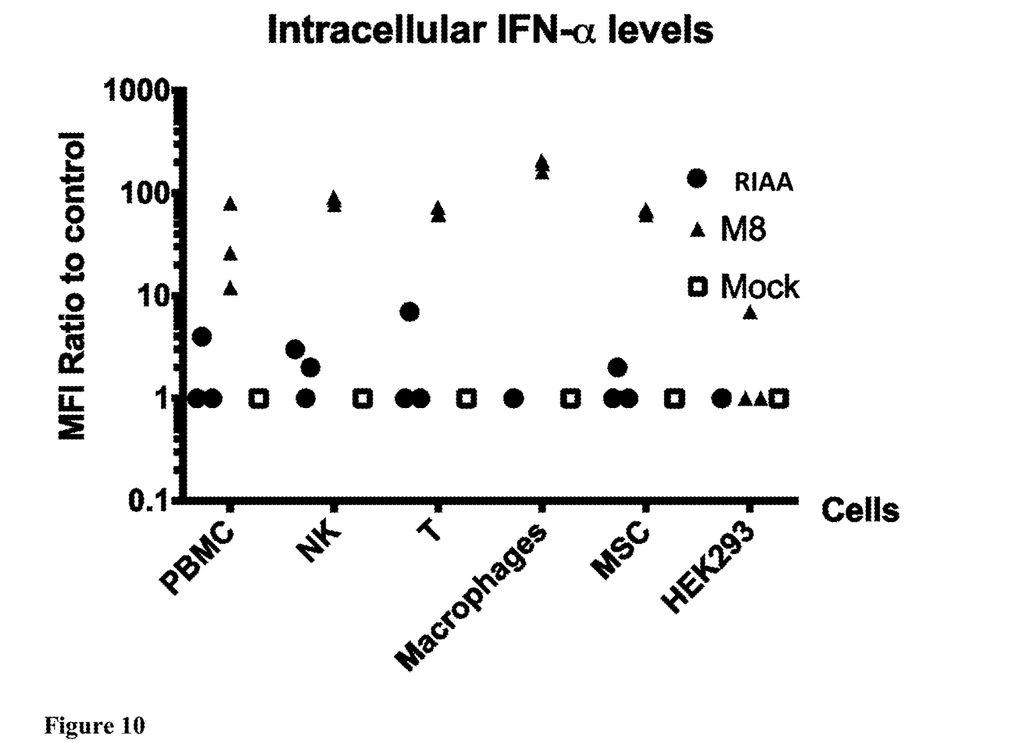
FIG. 10 is graph showing the absence of a interferon response in cells treated with RIG I agonist A.

Methods: Intracellular cytokine staining in primary cells was performed after 5 h after various RIG-I stimulations including mock control and M8. 10 µg/ml brefeldin A (Sigma-Aldrich) was added during the last 1 h. After the stimulation, cells were stained with CD40 (5C3; BD), and then fixed, permeabilized (CytoFIX-CytoPERM; BD), and stained with FITC-labeled mouse anti-human IFN-α mAb (MC-16; Genzyme). FITC-labeled goat anti-mouse IgG F(ab')2 (Becton Dickinson) was used as the secondary antibody for anti-IFN-α mAb after repermeabilization.
Results:

Referring to FIG. 10, the RIAA transfection did not significantly alter intracellular IFN-α levels compared to controls in any of the cell types tested. However, M8 electroporation yielded varying results depending on the cell type, suggesting that RIG-I induction in primary cells can vary on RNA sequence or structure.

These results are surprising because all known RIG-I agonists utilize viral mimicry. At this point in time, no one has generated an oligonucleotide sequence that can upregulate perforin and granzyme B and not upregulate a type-1 IFN. This is true of all known RIG I agonsists including viral RNAs and mimicking RNAsexcept RIAA. This is true of M5 and M8. This clearly shows that RIAA does not induce an IFN-Alpha response while up regulating the cytolytic proteins. The significance is that it doesn't induce a previously well published RIG-I response.

The lack of IFN upregulation is significant because the IFN-α response is the initiation step of the antiviral cascade. It starts viral defenses and attracts immune effectors. It is undesirable to attract the immune effectors and therefore cause an inflammatory response at the injection site.

The inflammatory response at the injection site is why known RIG I agonists are not desirable for systemic delivery. The inflammatory response is expected to be a dose response. For intratumoral injection, this inflammatory response would not be clinically significant.

Without being limited as to theory the inventor hypothesizes that this could be the result of a dual partial agonism of RIAA with TLR (maybe TRL7) and RIG-I. RIAA binds to RIG-I for certain. While it has not been shown that RIAA can bind to TLR, experiments will be conducted with CRISPR guide RNAs for all TLRs to test this on primary NK cells or cell lines.

Thus, while there have been shown and described and pointed out fundamental novel features of the present invention as applied to preferred embodiments thereof, it will be understood that various omissions and substitutions and changes in the form and details of the molecules illustrated, and in their operation, and in the methods of use described, may be made by those skilled in the art without departing from the spirit of the invention as broadly disclosed herein.

REFERENCES

Beljanski V, Chiang C, Kirchenbaum G A, Olagnier D, Bloom C E, Wong T, et al. (2015). Enhanced Influenza Virus-Like Particle Vaccination with a Structurally Optimized RIG-I Agonist as Adjuvant. *Journal of virology* 89(20): 10612-10624.

Bhat R, Watzl C (2007). Serial killing of tumor cells by human natural killer cells—enhancement by therapeutic antibodies. *PloS one* 2(3): e326.

Chiang C, Beljanski V, Yin K, Olagnier D, Ben Yebdri F, Steel C, et al. (2015). Sequence-Specific Modifications Enhance the Broad-Spectrum Antiviral Response Activated by RIG-I Agonists. *Journal of virology* 89(15): 8011-8025

Goubau D, Schlee M, Deddouche S, Pruijssers A J, Zillinger T, Goldeck M, et al. (2014). Antiviral immunity via RIG-I-mediated recognition of RNA bearing 5'-diphosphates. *Nature* 514(7522): 372-375.

Grandvaux N, Servant M J, tenOever B, Sen G C, Balachandran S, Barber G N, et al. (2002). Transcriptional profiling of interferon regulatory factor 3 target genes: direct involvement in the regulation of interferon-stimulated genes. *Journal of virology* 76(11): 5532-5539.

Henkart P A (1985). Mechanism of lymphocyte-mediated cytotoxicity. *Annu Rev Immunol* 3: 31-58.

Hornung V, Ellegast J, Kim S, Brzozka K, Jung A, Kato H, et al. (2006). 5'-Triphosphate RNA is the ligand for RIG-I. *Science* 314(5801): 994-997.

Karre K, Ljunggren H G, Piontek G, Kiessling R (1986). Selective rejection of H-2-deficient lymphoma variants suggests alternative immune defence strategy. *Nature* 319(6055): 675-678.

Kawai T, Takahashi K, Sato S, Coban C, Kumar H, Kato H, et al. (2005). IPS-1, an adaptor triggering RIG-I- and Mda5-mediated type I interferon induction. *Nature immunology* 6(10): 981-988.

Lanier L L (2001). On guard—activating NK cell receptors. *Nature immunology* 2(1): 23-27.

Liu S Y, Sanchez D J, Cheng G (2011). New developments in the induction and antiviral effectors of type I interferon. *Current opinion in immunology* 23(1): 57-64.

Shu D, Shu Y, Haque F, Abdelmawla S, Guo P (2011). Thermodynamically stable RNA three-way junction for constructing multifunctional nanoparticles for delivery of therapeutics. *Nature nanotechnology* 6(10): 658-667.

Takeuchi O, Akira S (2010). Pattern recognition receptors and inflammation. *Cell* 140(6): 805-820

---

I claim:

1. A Rig I agonist comprising an RNA molecule having a central hairpin and an internal loop, and which produces no interferon response when administered, wherein the RNA molecule comprises SEQ ID NO 1.

2. A method of increasing the levels of granzyme B and/or perforin in a cytotoxic cell comprising administering the Rig I agonist of claim 1 to such cytotoxic cell with or without IL2.

3. The method of claim 2, wherein the granzyme B levels are increased by a factor of 800-1100 times the level of an untreated cell.

4. The method of claim 3, wherein the cytotoxic cell is a natural killer cell, an NK 92 cell, a CD8 cell, or a lymphocyte.

5. The method of claim 2, wherein the perforin levels are increased by a factor of 1600-2000 times the level of an untreated cell.

6. The method of claim 5, wherein the cytotoxic cell is a natural killer cell, an NK 92 cell, a CD8 cell, or a lymphocyte.

7. A method of treating a disease in a patient in need thereof comprising administering an effective amount of the Rig I agonist of claim 1 to a patient in need thereof, wherein the disease is selected from cancer and infectious disease.

8. An isolated cytotoxic cell comprising at least one RNA molecule comprising SEQ ID NO: 1.

9. A method of treating a patient having a disease that is treatable with adoptive cell transfer comprising administering a cell which has been treated with the Rig I agonist of claim 1 to the patient.

10. The method of claim 9, wherein the patient also receives IL2.

11. A method of increasing the viability or engraftment of stem cells and/or enhancing stem cell expansion, delivery or therapeutic benefit comprising contacting a stem cell with the Rig I agonist of claim 1, wherein the contacting is with or without IL2.

12. A method of extending survival time in a mammal having cancer comprising administering extracellular vesicles isolated from cytotoxic cells treated with the Rig I agonist of claim 1, wherein the administration is with or without IL2.

13. A method of boosting activation of a cytotoxic cell comprising administering the Rig I agonist of claim 1 together with at least one: Bispecific Killer cell Engager ("BIKEs"), Trispecific Killer cell Engager ("TRIKEs") or monoclonal antibody.

14. The method of claim 13, wherein the cytotoxic cell is selected from a natural killer cell, an NK 92 cell, a CD8 cell, or a lymphocyte.

15. A method of increasing immune response in a tumor microenvironment comprising the delivery of a Rig I agonist of claim 1 using targeted oncolytic viruses, viral vectors, monoclonal antibodies or ferrying and/or cell penetrating peptides or extracellular vesicles derived from Rig I agonist transfected cells.

16. The method of claim 15, wherein the cytotoxic cell is selected from a natural killer cell, an NK 92 cell, a CD8 positive cell, a TALL cell, or a lymphocyte.

17. A method of increasing CD90 expression in mesenchymal stromal cells or a hematopoietic stem cell comprising administering the Rig I agonist of claim 1 to the mesenchymal stromal cells or the hematopoietic stem cell.

\* \* \* \* \*

SEQUENCE LISTING

<160> NUMBER OF SEQ ID NOS: 5

<210> SEQ ID NO 1
<211> LENGTH: 55
<212> TYPE: RNA
<213> ORGANISM: Artificial Sequence
<220> FEATURE:
<223> OTHER INFORMATION: Synthetic RNA sequence

<400> SEQUENCE: 1
gacgaagacc acaaaccaga uaaaaauaau uuuuaucugg uuguuugucu ucguc    55

<210> SEQ ID NO 2
<211> LENGTH: 60
<212> TYPE: DNA
<213> ORGANISM: Artificial Sequence
<220> FEATURE:
<223> OTHER INFORMATION: Synthetic DNA sequence

<400> SEQUENCE: 2
gacgaagacc acaaaccag ataaaaaata atttttatc tggttttgtg gtcttcgtcc    60

<210> SEQ ID NO 3
<211> LENGTH: 99
<212> TYPE: DNA
<213> ORGANISM: Artificial Sequence
<220> FEATURE:
<223> OTHER INFORMATION: Artificial DNA

```
<400> SEQUENCE: 3
gacgaagacc acaaaaccag ataaaaaaaa aaaaaaaaaa aaaaaaaata attttttttt      60
tttttttttt tttttttatc tggttttgtg gtcttcgtc                            99

<210> SEQ ID NO 4
<211> LENGTH: 140
<212> TYPE: RNA
<213> ORGANISM: Artificial Sequence
<220> FEATURE:
<223> OTHER INFORMATION: Artificial RNA

<400> SEQUENCE: 4
gacgaagacc acaaaaccag auaaaaaauu auuuuuuauc ugguuuugug gucuucgucu      60
auagugaguc guauuaauuu cgaaauuaau acgacucacu auagacgaag accacaaaac    120
cagauaaaaa auaauuuuuu                                                140

<210> SEQ ID NO 5
<211> LENGTH: 180
<212> TYPE: RNA
<213> ORGANISM: Artificial Sequence
<220> FEATURE:
<223> OTHER INFORMATION: Artificial RNA

<400> SEQUENCE: 5
gaaauuaaua cgacucacua uagacgaaga ccacaaaacc agauaaaaaa aaaaaaaaaa      60
uaauuuuuuu uuuuuuuuua ucugguuuug uggucuucgu cgaaauuaau acgacucacu    120
auagacgaag accacaaaac cagauaaaaa aaaaaaaaaa aaaaaaaaaa auaauuuuuu    180
```